United States Patent [19]

Krüger et al.

[11] Patent Number: 4,511,562
[45] Date of Patent: Apr. 16, 1985

[54] (THIO)(DITHIO-PHOSPHATES(PHOSPHONATES), PROCESSES FOR THEIR PREPARATION, AND THEIR USE IN PEST-COMBATING AGENTS

[75] Inventors: Bernd-Wieland Krüger, Wuppertal; Wolfgang Behrenz, Overath, both of Fed. Rep. of Germany

[73] Assignee: Bayer Aktiengesellschaft, Leverkusen, Fed. Rep. of Germany

[21] Appl. No.: 404,249

[22] Filed: Aug. 2, 1982

[30] Foreign Application Priority Data

Aug. 13, 1981 [DE] Fed. Rep. of Germany ....... 3131980
Jun. 7, 1982 [DE] Fed. Rep. of Germany ....... 3221479

[51] Int. Cl.³ .................... A01N 57/00; A01N 57/16; A01N 57/26; A01N 65/00
[52] U.S. Cl. .................................... 514/112; 260/940
[58] Field of Search ............... 424/210, 200, 202, 203, 424/186, 187, 192, 193; 260/940

[56] References Cited

U.S. PATENT DOCUMENTS 2,965,533 12/1960 Whetstone .......................... 424/210

FOREIGN PATENT DOCUMENTS 1047776 12/1958 Fed. Rep. of Germany .

OTHER PUBLICATIONS

Derwert Japanese, 1/9/69–1/14/69, vol. 8, No. 2.
Derwert Japanese, 3/14/68–3/19/68, vol. 7, No. 11.
Chemical Abstracts, vol. 52, pp. 8937–8940.

Primary Examiner—Allen J. Robinson
Attorney, Agent, or Firm—Sprung Horn Kramer & Woods

[57] ABSTRACT

Pesticidal dicyanohydrin (thiono)(dithio)-phosphates(-phosphonates) of the general formula

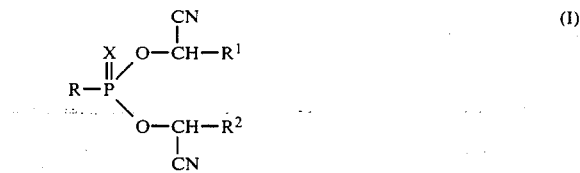

in which
X represents oxygen or sulphur,
R represents an optionally substituted radical selected from alkyl, alkenyl, alkinyl, aryl, aralkyl, alkoxy, aryloxy, aralkoxy, alkylthio, arylthio, aralkylthio, alkylamino (mono- and dialkylamino), arylamino and aralkylamino, and
$R^1$ and $R^2$ are identical or different and individually represent a hydrogen atom, an optionally substituted radical selected from alkyl, alkenyl, alkinyl, cycloalkyl, cycloalkenyl, aralkyl, aralkenyl and aryl, or an optionally substituted heterocyclic radical, are new and are particularly effective in combating pests, such as insects and acarids, in synergistic combinations with other compounds which are active against arthropods.

11 Claims, No Drawings

(THIO)(DITHIO-PHOSPHATES(PHOSPHONATES), PROCESSES FOR THEIR PREPARATION, AND THEIR USE IN PEST-COMBATING AGENTS

The present invention relates to certain new dicyanohydrin (thiono)(dithio)-phosphates(phosphonates) to processes for their production, and to their use, alone as agents for combating pests, and in pest-combating synergistic combinations, in particular for combating arthropods, especially insects and arachnida, such as mites.

Synergistic mixtures of insecticidal active compounds, for example of pyrethroids, with certain methylenedioxyphenyl derivatives, for example piperonyl butoxide, as synergists have already been disclosed (see, for example, K. Naumann, Chemie der Pflanzenschutz- und Schädlingsbekämpfungsmittel (Chemistry of Plant Protection Agents and Pest-Combating Agents), Springer Verlag Berlin, Volume 7 (1981), pages 3–6). However, the activity of such preparations in practice is not always completely satisfactory.

The present invention now provides, as new compounds, dicyanohydrin (thiono)(dithio)-phosphates(phosphonates) of the general formula

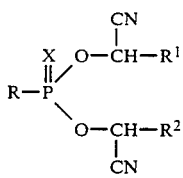   (I)

in which

X represents oxygen or sulphur,

R represents an optionally substituted radical selected from alkyl, alkenyl, alkinyl, aryl, aralkyl, alkoxy, aryloxy, aralkoxy, alkylthio, arylthio, aralkylthio, alkylamino(mono- and dialkylamino), arylamino and aralkylamino, and $R^1$ and $R^2$ are identical or different and individually represent a hydrogen atom, an optionally substituted radical selected from alkyl, alkenyl, alkinyl, cycloalkyl, cycloalkenyl, aralkyl, aralkenyl and aryl, or an optionally substituted heterocyclic radical.

The compounds of formula (I) according to the present invention can be used particularly effectively as synergists in pest-combating agents which additionally contain substances which are active against arthropods, preferably against insects and arachnida, in particular against insects.

According to the present invention we further provide a process for the production of a compound according to the present invention, characterised in that (a) a (thiono)(dithio)-phosphoric(phosphonic) acid cyanohydrin ester-chloride of the general formula

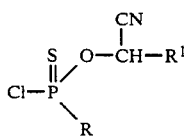   (II)

in which R and $R^1$ have the meanings given above, is reacted with an aldehyde of the general formula $R^2$—CHO   (III)

in which $R^2$ has the meaning given above, in the presence of an approximately equimolar amount of a water-soluble cyanide, in the presence of a catalyst, in the presence of water and a virtually water-immiscible diluent, at a temperature between 0° and 80° C., or (b) a thio-phosphoric(phosphonic) acid dichloride of the general formula

   (IV)

in which R has the meaning given above, is reacted either with an aldehyde of the general formula $R^1$CHO   (V)

in which $R^1$ has the meaning given above, and/or with an aldehyde of the general formula $R^2$CHO   (III)

in which $R^2$ has the meaning given above, in the presence of a water-soluble cyanide, in the presence of a catalyst, in the presence of water and a virtually water-immiscible solvent, at a temperature between 0° and 80° C., or (c) a phosphonic(phorphoric) acid dichloride of the general formula

   (VI)

in which R has the meaning given above, is reacted with a substituted acetonitrile of the general formula

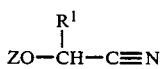   (VII)

in which $R^1$ has the meaning given above, and

Z represents a hydrogen atom or an alkali metal ion, and/or with a substituted acetonitrile of the general formula

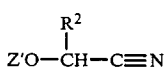   (VIII)

in which $R^2$ has the meaning given above, the

Z′ represents a hydrogen atom or an alkali metal ion, if appropriate in the presence of an acid acceptor and, if appropriate, in the presence of a diluent, at a temperature between −80° C. and +80° C.

The present invention yet further provides a new pesticidal composition containing as active ingredients, (1) a compound according to the present invention of formula (I), and (2) another compound which is active against arthropods, alone or in admixture with a solid or liquid or liquefied gaseous diluent or carrier.

Surprisingly, the action, against arthropods, of the new active compound combinations according to the invention is substantially higher than the action of the individual components or the sum of the actions of the individual components. Furthermore, it is substantially higher than the action of active compound combinations containing the known synergistic compound piperonyl butoxide. In addition, the new dicyanohydrin (thiono)(dithio)-phosphates-(phosphonates) of the present invention exhibit excellent synergistic activity not only in the case of a single active compound class, but in the case of active compounds from the most diverse chemical groups of substances.

Suitable substances which are active against arthropods are virtually any of customary active compounds (see, for example, K. H. Büchel, Pflanzenschutz und Schädlungsbekämpfungsmittel (Plant Protection and Pest-Combating Agents), Thieme Verlag Stuttgart, 1977, and Farm Chemicals Handbook 1979, Meister Publishing Company, Willougby, 1979).

Optionally substituted alkyl radicals of R, $R^1$ and $R^2$ are straight-chain or branched alkyl radical having preferably 1 to 20, more preferably 1 to 10, especially 1 to 5, carbon atoms. Optionally substituted methyl, ethyl, n- and iso-propyl, n-, iso- and tert.-butyl may be mentioned as examples.

Optionally substituted alkenyl radicals of R, $R^1$ and $R^2$ are straight-chain or branched alkenyl radicals having preferably 2 to 5, especially 2 to 4, carbon atoms. Optionally substituted ethenyl, propen-1-yl, propen-2-yl and buten-3-yl may be mentioned as examples.

Optionally substituted alkinyl radicals of R, $R^1$ and $R^2$ are straight-chain or branched alkinyl radicals having preferably 2 to 5, especially 2 to 4, carbon atoms. Optionally substituted ethinyl, propin-1-yl, propin-2-yl and butin-3-yl may be mentioned as examples.

Optionally substituted cycloalkyl of $R^1$ and $R^2$ are mono-, bi- and tricyclic cycloalkyl radicals having preferably 3 to 8, especially 3, 5 or 6, carbon atoms. Optionally substituted cyclopropyl, cyclobutyl, cyclopentyl, cyclohexyl, cycloheptyl, bicyclo[2,2,1]-heptyl, bicyclo[2,2,2]-octyl and adamantyl may be mentioned as examples.

Optionally substituted cycloalkenyl radicals of $R^1$ and $R^2$ are preferably monocyclic cycloalkenyl having 5 or 6 carbon atoms and 1 or 2 double bonds.

The optionally substituted alkoxy radical of R is a straight-chain or branched alkoxy radical having preferably 1 to 6, especially 1 to 4, carbon atoms. Optionally substituted methoxy, ethoxy, n- and iso-propoxy and n-, iso- and tert.-butoxy may be mentioned as examples.

The optionally substituted alkylthio radical of R is a straight-chain or branched alkylthio radical having preferably 1 to 6, especially 1 to 4, carbon atoms. Optionally substituted methylthio, ethylthio, n- and iso-propylthio, n-, iso- and tert.-butylthio may be mentioned as examples.

Optionally substituted aryl radicals of R, $R^1$ and $R^2$ are aryl radicals having preferably 6 to 10 carbon atoms in the aryl part. Optionally substituted phenyl or naphthyl, in particular phenyl, may be mentioned as examples.

Optionally substituted aralkyl radicals of R, $R^1$ and $R^2$ are aralkyl radicals, being optionally substituted in the aryl part and/or alkyl part and having preferably 6 or 10, especially 6, carbon atoms in the aryl part and preferably 1 or 4, especially 1 or 2, carbon atoms in the alkyl part, it being possible for the alkyl part to be straight-chain or branched. Optionally substituted benzyl and phenylethyl may be mentioned as examples.

Optionally substituted aralkenyl radicals of $R^1$ and $R^2$ correspond in their aryl part to the aralkyl radicals of $R^1$ and $R^2$. They contain, in the alkenyl part, preferably 2 to 6, especially 2 or 3, carbon atoms and preferably 1 or 2, more preferably 1, double bond.

The optionally substituted aryloxy, arylthio and arylamino radical of R contains preferably 6 or 10 carbon atoms in the aryl part; phenoxy, naphthyloxy, phenylthio and naphthylthio, phenylamino and naphthylamino, preferably phenoxy, phenylthio and phenylamino, being mentioned.

The optionally substituted aralkoxy, aralkylthio and aralkylamino radical of R contains, in the aryl part, preferably 5 or 10 carbon atoms; phenyl being mentioned as being particularly preferred. The alkyl part is branched or straight-chain and contains preferably 1 to 4, in particular 1 or 2, carbon atoms. The benzyl radical is particularly preferred as the aralkyl part.

In the optionally substituted alkylamino radical R, the amino group contains 1 or 2 alkyl groups, each of which can be straight-chain or branched and contains preferably 1 to 5, in particular 1 to 3, carbon atoms; methyl, ethyl, n- and iso-propyl being mentioned. Monomethylamino and dimethylamino may be mentioned as examples.

Optionally substituted heterocyclic radicals of $R^1$ and $R^2$ are heteroparaffinic, heteroaromatic and heteroolefinic preferably 5-membered to 7-membered, more preferably 5-membered or 6-membered, rings having preferably 1 to 3, especially 1 or 2, identical or different heteroatoms, such as oxygen, sulphur or nitrogen. Optionally substituted pyrrolidinyl, piperidinyl, furyl, thiophenyl, pyrazolyl, imidazolyl, 1,2,3- and 1,2,4-triazolyl, oxazolyl, isoxazolyl, thiazolyl, isothiazolyl, 1,2,3-, 1,3,4-, 1,2,4- and 1,2,5-oxadiazolyl, azepinyl, pyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl may be mentioned as examples.

The substituted radicals mentioned in the definition of R, $R^1$ and $R^2$ can carry one or more, preferably 1 to 3, especially 1 or 2, identical or different substituents. The following may be listed as examples of substituents: alkyl having preferably 1 to 4, especially 1 or 2, carbon atoms, such as methyl, ethyl, n- and iso-propyl and n-, iso- and tert.-butyl; alkoxy having preferably 1 to 4, especially 1 or 2, carbon atoms, such as methoxy, ethoxy, n- and iso-propoxy and n-, iso- and tert.-butoxy; alkylthio having preferably 1 to 4, especially 1 or 2, carbon atoms, such as methylthio, ethylthio, n- and iso-propylthio and n-, iso- and tert.-butylthio; halogenoalkyl having preferably 1 to 4, especially 1 or 2, carbon atoms and preferably 1 to 5, especially 1 to 3, halogen atoms, the halogen atoms being identical or different and being preferably fluorine, chlorine or bromine, especially fluorine, such as trifluoromethyl; halogen, preferably fluorine, chlorine, bromine and iodine, especially chlorine and bromine; cyano; nitro; alkoxycarbonyl having preferably 2 to 4, especially 2 or 3, carbon atoms, such as methoxycarbonyl and ethoxycarbonyl and phenoxybenzyloxycarbonyl. In the case of radicals containing aryl parts, the aryl parts, for example the phenyl rings, can be substituted by alkylenedioxy groups which contain preferably 1 to 3, especially 1 or 2, carbon atoms and can be substituted by 1 to 4 identical or different halogen atoms (fluorine, chlorine, bromine and iodine).

In the definition of the radicals of the compounds of the formulae (I) to (XIa), halogen denotes in each case (unless stated otherwise) fluorine, chlorine, bromine and iodine, preferably fluorine, chlorine and bromine.

Preferred compounds of the formula (I) are those in which

X represents oxygen or sulphur,

R represents an optionally halogen-substituted radical selected from $C_1$ to $C_5$ alkyl, $C_2$ to $C_5$ alkenyl, $C_2$ to $C_5$ alkinyl, phenyl, benzyl, $C_1$ to $C_5$ alkoxy, phenoxy, benzyloxy, $C_1$ to $C_5$ alkylthio, phenylthio, benzylthio, mono- or di-($C_1$ to $C_5$ alkyl)amino, phenylamino and benzylamino, and $R^1$ and $R^2$ are identical or different and individually represent a hydrogen atom, an alkyl radical which has 1 to 20 carbon atoms (and is optionally substituted by halogen, cyano, $C_1$ to $C_4$ alkoxy or $C_1$ to $C_4$ alkylthio), an optionally halogen-substituted $C_2$ to $C_5$ alkenyl or $C_2$ to $C_5$ alkinyl radical, a $C_3$ to $C_8$ cycloalkyl radical (which is optionally substituted by $C_1$ to $C_4$ alkyl, $C_1$ to $C_4$ alkoxycarbonyl, phenoxybenzyloxycarbonyl and/or halogen), a phenyl-$C_1$ to $C_4$ alkyl radical(which is optionally substituted by halogen, $C_1$ to $C_4$ alkyl or $C_1$ to $C_4$ alkoxy), a phenyl radical which is optionally substituted by halogen, cyano, nitro, $C_1$ to $C_4$ alkyl, $C_1$ to $C_4$ alkoxy, $C_1$ to $C_4$ alkylthio or trifluoromethyl and/or by optionally halogen-substituted $C_1$ or $C_2$ alkylenedioxy) or a furyl, thienyl or pyridyl radical.

The invention relates in particular to compounds of the formula (I), in which

X represents oxygen or sulphur,

R represents an optionally fluorine-substituted or optionally chlorine-substituted radical selected from $C_1$ to $C_5$ alkyl, phenyl, $C_1$ to $C_5$ alkoxy, phenoxy, benzyloxy, $C_1$ to $C_5$ alkylthio, phenylthio, benzylthio and mono- or di-($C_1$ to $C_5$ alkyl)-amino, and $R^1$ and $R^2$ are identical or different and individually represent a hydrogen atom, an alkyl radical which has 1 to 10 carbon atoms (and is optionally substituted by fluorine, chlorine, methoxy or methylthio), a $C_2$ to $C_5$ alkenyl or $C_3$ to $C_6$ cycloalkyl radical, an optionally chlorine-substituted phenyl-$C_1$ or $C_2$ alkyl radical, a phenyl radical (which is optionally substituted by fluorine, chlorine, cyano, nitro, methyl, methoxy, trifluoromethyl and/or methylenedioxy) or a thienyl or pyridyl radical.

If, for example, O-ethyl-O-(1-cyano-2-methylpropyl)thiophosphoric acid ester-chloride, acetaldehyde and sodium cyanide are used as starting materials in reaction variant (a), the reacton of these compounds can be represented by the following equation:

CH$_3$—CHO + NaCN +

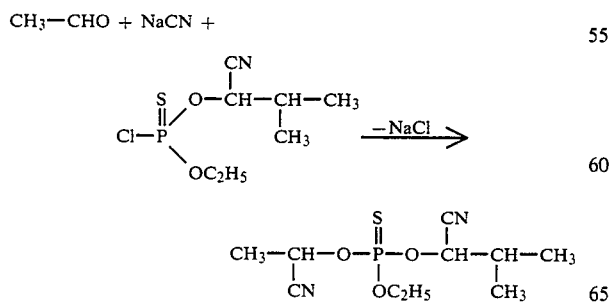

If, for example, ethanethiophosphonic acid dichloride, acetaldehyde and sodium cyanide are used as starting materials in reaction variant (b) according to the invention, the reaction of these compounds can be represented by the following equation:

CH$_3$—CHO + NaCN + 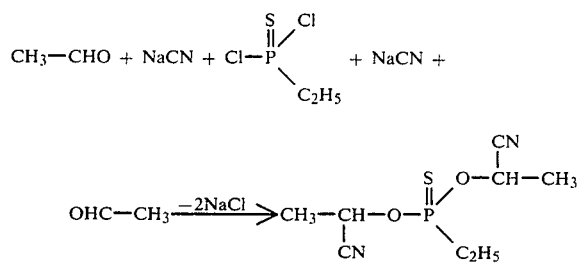 + NaCN +

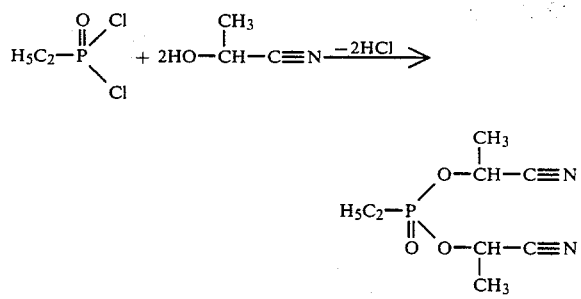

If, for example, ethanephosphonic acid dichloride and 2-hydroxypropionic acid nitrile are used as starting materials in reaction variant (c), the reaction of these compounds can be represented by the following equation:

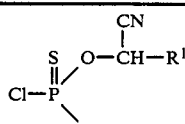

Preferred (thiono)(dithio)-phosphoric(phosphonic) acid cyanohydrin ester-chlorides of formula (II) to be used as starting materials in reaction variant (a) according to the invention are those in which R and $R^1$ represent those radicals which are given above for R and $R^1$ in the definition of preferred and particularly preferred compounds of formula (I).

The following may be mentioned as examples of the compounds of the formula (II):

TABLE 1

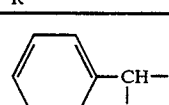

| R | $R^1$ |
|---|---|
| $C_2H_5O$ | 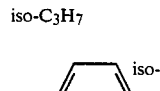 |
| n-$C_3H_7S$ | iso-$C_3H_7$ |
| $C_2H_5O$ | 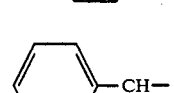 |
| n-$C_3H_7S$ | |

TABLE 1-continued $$\text{(II)} \quad \underset{\underset{R}{\overset{Cl-P}{\big|}}}{\overset{S}{\|}}\text{O}-\overset{\overset{CN}{|}}{\text{CH}}-R^1$$

| R | R¹ |
|---|---|
| $C_2H_5O$ | Cl—C₆H₄— (4-chlorophenyl) |
| $N(CH_3)_2$ | C₆H₅—CH(CH₃)— |
| $C_2H_5O$ | iso-$C_3H_7$ |
| C₆H₅— | iso-$C_3H_7$ |
| $CH_3$ | iso-$C_3H_7$ |
| $C_2H_5$ | iso-$C_3H_7$ |
| $C_2H_5$ | Cl—C₆H₄— |
| $C_2H_5$ | $C_2H_5$ |
| $C_2H_5$ | $CH_3$ |
| n-$C_3H_7$S | $CH_3$ |
| $C_2H_5O$ | $CH_3$ |
| $CH_3$ | $CH_3$ |
| $C_2H_5O$ | C₆H₅—CH(CH₃)— |
| iso-$C_3H_7$S | $CH_3$ |
| n-$C_3H_7$S | $C_2H_5$ |

The compounds of the formula (II) can be prepared by the reaction of an aldehyde with a thio-phosphoric(-phosphonic) acid dichloride in the presence of an equimolar amount of a water-soluble cyanide (such as sodium cyanide) in the presence of water and a virtually water-immiscible organic solvent (such as n-hexane), and, if appropriate, in the presence of a catalyst (such as tetrabutylammonium bromide) which is usually used for the phase transfer of reactants in reactions in two-phase systems comprising water and water-immiscible organic solvents, at a temperature between 0° and 80° C.

Preferred aldehydes of formulae (III) and (V) further to be used as starting materials in reaction variants (a) and (b) according to the invention are those, in which $R^2$ and $R^1$ represent those radicals which are given above for $R^2$ and $R^1$ in the definitions of preferred and particularly preferred compounds of formula (I).

The following may be mentioned as examples of the compounds of the formula (III) or (V): formaldehyde, acetaldehyde, propionaldehyde, butyraldehyde, iso-butyraldehyde, valeraldehyde, iso-valeraldehyde, sec.-valeraldehyde, caproaldehyde, iso-caproaldehyde, sec.-caproaldehyde, pival aldehyde, acrolein, crotonaldehyde, methoxyacetaldehyde, methylthioacetaldehyde, cyclohexanecarbaldehyde, benzaldehyde, 4-chloro-benzaldehyde, 4-methyl-benzaldehyde, 3,4-methylenedioxy-benzaldehyde, 4,5-methylenedioxy-2-nitrobenzaldehyde, phenylacetaldehyde, α-phenylpropionaldehyde, thiophene-2-carbaldehyde, thiophene-3-carbaldehyde, pyridine-2-carbaldehyde, and pyridine-3-carbaldehyde.

The starting compounds of the formulae (III) and (V) are known.

Examples of water-soluble cyanides which can be used in reaction variant (a) according to the invention are alkali metal cyanides (such as sodium cyanide and potassium cyanide); sodium cyanide is preferably used.

Water-immiscible solvents which are employed, as preferences, in reaction variant (a) according to the invention are hydrocarbons, in particular straight-chain or branched alkanes or cycloalkanes having 5 to 10 carbon atoms (such as n-pentane, n-hexane, n-heptane, n-octane, n-nonane, n-decane, 2-methylpentane, 3-methylpentane, 2-methylhexane, 2,2,4-trimethylpentane, cyclohexane or methylcyclohexane) and methylbenzenes (such as toluene or xylenes), and also mixtures of these hydrocarbons.

Catalysts which are used in process variant (a) according to the invention are preferably compounds which are usually employed for the phase transfer of reactants in reactions in two-phase systems comprising water and water-immiscible organic solvents (phase-transfer catalysts). Preferred compounds of this type are, in particular, tetraalkyl- and trialkyl-aralkyl-ammonium salts having preferably 1 to 10, especially 1 to 8, carbon atoms per alkyl group, preferably phenyl as the aryl constituent of the aralkyl group, and preferably 1 to 4, especially 1 or 2, carbon atoms in the alkyl part of the aralkyl groups. Suitable compounds are, in particular, the halides (such as the chlorides, bromides and iodides); preferably the chlorides and bromides. Tetrabutylammonium bromide, benzyltriethylammonium chloride and methyltrioctylammonium chloride may be mentioned as examples.

In reaction variant (a) according to the invention, the reaction temperature is kept between 0° and 80° C., preferably between 0° and 30° C. The process is preferably carried out under atmospheric pressure.

In general between 0.6 and 1.1 mol, preferably 0.75 to 1.0 mol, of aldehyde of the formula (III), between 1.0 and 1.5 mol, preferably 1.1 to 1.3 mol, of cyanide and, if appropriate, between 0.001 and 0.05 mol, preferably 0.01 to 0.03 mol, of catalyst are employed per mol of thiono(dithio)phosphoric(phosphonic) acid cyanohydrin ester-chloride of the formula (II).

In a preferred embodiment of reaction variant (a) according to the invention, the starting compounds of the formulae (II) and (III), the catalyst and the cyanide are dissolved in the water-immiscible solvent, and water is slowly added to this solution, the reaction temperature being brought to 0° to 10° C., if necessary initially by external cooling. The reaction mixture is then stirred for several hours at about 20° C.

To work up the mixture, it is diluted, if appropriate, with further water-immiscible solvent, and the organic phase is separated off, washed with water, dried and filtered. The filtrate is freed of solvent by distillation under reduced pressure, the crude product being obtained as an oily residue.

Preferred thio-phosphoric(phosphonic) acid dichlorides of formula (IV) to be used as starting materials in reaction variant (b) according to the invention are those in which R represents those radicals which are given above for this radical in the definition of the preferred and particularly preferred compounds of formula (I).

The following may be mentioned as examples of the compounds of the formula (IV): methane-, ethane-, propane-, butane- and benzene-thiophosphonic acid dichloride; O-methyl-, O-ethyl, O-n- and O-iso-propyl-, O-n-, O-iso and O-sec.-butyl-, O-phenyl- and O-benzyl-thionophosphoric acid ester-dichloride; S-methyl-, S-ethyl-, S-n- and S-iso-propyl-, S-n-, S-iso- and S-sec.-butyl-, S-phenyl- and S-benzyl-dithiophosphoric acid ester-dichloride.

The compounds of the formula (IV) are known and/or can be prepared in a customary manner according to processes which are in themselves known (see Methoden der organischen Chemie (Methods of Organic Chemistry) (Houben-Weyl-Müller), 4th Edition, Volume 12/1 (1963), pages 387–406 and pages 552–557; Volume 12/2 (1964), pages 212–225, 590–594 and 682–683; Thieme-Verlag Stuttgart).

Preferred water-soluble cyanides which can be used in reaction variant (b) according to the invention are the cyanides which have already been mentioned for reaction variant (a).

Preferred solvents for the reaction according to reaction variant (b) are the solvents which have already been mentioned for reaction variant (a).

Preferred catalysts for the reaction according to reaction variant (b) are the catalysts which have already been mentioned for reaction variant (a).

In process (b) according to the invention, the reaction temperature is kept between 0° and 80° C., preferably between 0° and 30° C. The process is preferably carried out under atmospheric pressure.

In general between about 2.5 and 4.0 mol, preferably between about 3.0 and 3.5 mol, of aldehyde of the formula (III) or (V), between about 2.0 and 3.0 mol, preferably about 2.2 to 2.6 mol, of cyanide and, if appropriate, between about 0.002 and 0.1 mol, preferably between 0.02 and 0.06 mol, of catalyst are employed per mol of thiophosphoric(phosphonic) acid dichloride of the formula (IV).

In a preferred embodiment of reaction variant (b) according to the invention, the starting compounds of the formulae (IV) and (V) or (III), the catalyst and the cyanide are dissolved in the water-immiscible solvent, and water is slowly added to this solution, the reaction temperature being brought to 0° to 5° C., if necessary initially by external cooling. The reaction mixture is then stirred for several hours at about 20° C.

To work up the mixture, it is diluted, if appropriate, with further water-immiscible solvent, and the organic phase is separated off, washed with water, dried and filtered. The filtrate is freed of solvent by distillation under reduced pressure, the crude product being obtained as as oily residue.

Preferred phosphonic(phosphoric) acid dichlorides of formula (VI) to be used as starting materials in reaction variant (c) according to the invention are those in which R represents those radicals which have already been given above for R in the definition of preferred and particularly preferred compounds of formula (I).

The following may be mentioned as examples of the compounds of the formula (VI): methane-, ethane-, propane-, butane- and benzene-phosphonic acid dichloride; O-methyl-, O-ethyl-, O-n- and O-iso-propyl-, O-n-, O-iso- and O-sec-butyl-, O-phenyl- and O-benzyl-phosphoric acid ester-dichloride; S-methyl-, S-ethyl, S-n- and S-iso-propyl-, S-n-, S-iso- and S-sec.-butyl-, S-phenyl- and S-benzyl-thiophosphoric acid ester-dichloride.

The compounds of the formula (VI) are known and/or can be prepared in a customary manner according to processes which are in themselves known (see Methoden der organischen Chemie (Methods of Organic Chemistry) (Houben-Weyl-Müller), 4th Edition, Volume 12/1 (1963), pages 387 et seq.; Volume 12/2 (1964), pages 212–225, page 383 and page 596; Thieme-Verlag Stuttgart).

Preferred substituted acetonitriles or their alkali metal salts of formulae (VII) and (VIII) further to be used as starting materials in reaction variant (c) according to the invention are those in which $R^1$ and $R^2$ represent those radicals which are given above for $R^1$ and $R^2$, respectively, in the definition of preferred and particularly preferred compounds of formula (I), and Z or Z' represents a hydrogen atom or a lithium, sodium or potassium ion.

The following may be mentioned as examples of the compounds of the formula (VII) or (VIII): hydroxyacetonitrile, 2-hydroxy-propanenitrile, 2-hydroxy-butanenitrile, 2-hydroxy-pentanenitrile, 2-hydroxy-3-methylbutanenitrile, 2-hydroxy-hexanenitrile, 2-hydroxy-3-methyl-pentanentirile, 2-hydroxy-4-methyl-pentanenitrile, 2-hydroxy-heptanenitrile, 2-hydroxy-3-methyl-hexanenitrile, 2-hydroxy-4-methyl-hexanenitrile, 2-hydroxy-octanenitrile, 2-hydroxy-3-methyl-heptanenitrile, 2-hydroxy-4-methyl-heptanenitrile, 2-hydroxy-3,3-dimethyl-butanenitrile, 2-hydroxy-4-butenenitrile, 2-hydroxy-3-pentenenitrile, 2-hydroxy-2-methoxy-acetonitrile, 2-hydroxy-2-methylthio-acetonitrile, 2-cyclohexyl-2-hydroxyacetonitrile, 2-hydroxy-2-phenylacetonitrile, 2-(4-chlorophenyl)-2-hydroxyacetonitrile, 2-(4-methylphenyl)-2-hydroxyacetonitrile, 2-(3,4-methylenedioxyphenyl)-2-hydroxyacetonitrile, 2-(4,5-methylenedioxy-2-nitrophenyl)-2-hydroxyacetonitrile, 2-hydroxy-3-phenyl-propanenitrile, 2-hydroxy-2-phenyl-propanenitrile, 2-hydroxy-2-(thien-2-yl)-acetonitrile, 2-hydroxy-2-(thien-3-yl)-acetonitrile, 2-hydroxy-2-(pyrid-2-yl)-acetonitrile and 2-hydroxy-2-(pyrid-3-yl)-acetonitrile, and the alkali metal salts, such as lithium, sodium and potassium salts, of these compounds.

The starting compounds of the formula (VII) or (VIII) are known, or can be prepared in a customary manner according to processes which are in themselves known (see Metoden der organischen Chemie (Methods of Organic Chemistry) (Houben-Weyl-Müller), 4th Edition, Volume 8/3 (1952), pages 274–278; Thieme-Verlag Stuttgart).

Virtually any of the inert organic solvents are suitable diluents in reaction variant (c). These include, in particular, aliphatic and aromatic, optionally halogenated hydrocarbons (such as pentane, hexane, heptane, cyclohexane, petroleum ether, petrol, ligroin, benzene, toluene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), (such as methyl acetate and ethyl acetate), nitriles (such as acetonitrile and propionitrile), amides (such as dimethylformamide, dimethylacetamide and N-methyl-pyrrolidone) and dimethyl-sulphoxide, tetramethylenesulphone and hexamethylene-phosphoric acid triamide.

Any of the customary acid-binding agents can be used as acid acceptors in reaction variant (c). These preferably include alkali metal carbonates and alkali metal alcoholates, such as sodium carbonate and potassium carbonate, sodium methylate, sodium ethylate, potassium methylate and potassium ethylate, and also aliphatic, aromatic or heterocyclic amines, for example trimethylamine, triethylamine, dimethylaniline, dimethylbenzylamine and pyridine.

In reaction variant (c), the reaction temperature is kept between −80° C. and +80° C., preferably between −60° C. and +30° C. The process is preferably carried out under atmospheric pressure.

In carrying out reaction variant (c), about 1.5 to 2.5 mol of substituted acetonitrile of the formula (VII) or (VIII) are preferably employed to about 1 mol of the compound of the formula (VI), the substituted acetonitrile, in the case in which Z or Z' represents a sodium, potassium or lithium ion, being preferably produced in situ from the corresponding hydroxyacetonitrile and a strong base, such as butyl-lithium, methyl-lithium, sodium, potassium, sodium hydride and sodium amide. The isolation of the end products is effected in a generally customary manner.

As indicated above, the new dicyanohydrin (thiono)(dithio)-phosphates(phosphonates) of the formula (I), when mixed with substances which have any desired constitution and are active against arthropods, exhibit powerful synergistic effects, thereby making it possible to use them in pest-combating agents.

Preferred active compound combinations comprise the new dicyanohydrin (thiono)(dithio)-phosphates(phosphonates) of the formula (I), as component (1), together with, as component (2), an arthropod-combating agent selected from one or more of
(A) carbamates and/or
(B) carboxylates, including the natural and synthetic pyrethroids, and/or
(C) phosphorus compounds (such as phosphates and phosphonates, including the thio and dithio compounds) and/or
(D) halgeno-(cyclo)-alkanes (such as hexachlorocyclohexane).

The synergistic action of the compounds of the formula (I), as component (1), is particularly preferably exhibited in the case of, as component (2),
(A) carbamates of the general formula

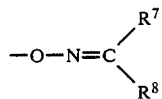
(IX)

in which
$R^3$ represents an optionally substituted carbocyclic or heterocyclic aromatic radical or an optionally substituted oxime radical (the radicals $R^3$ described further below being preferred),
$R^4$ represents a $C_1$ to $C_4$ alkyl radical, and
$R^5$ represents a hydrogen atom, a $C_1$ to $C_4$ alkyl radical or a radical Y,
in which
Y represents a radical of the general formula —CO—$R^6$, wherein $R^6$ represents a halogen atom, a $C_1$ to $C_4$ alkyl, $C_1$ to $C_4$ alkoxy, $C_3$ to $C_5$ alkenoxy, $C_3$ to $C_5$ alkinoxy, $C_1$ to $C_4$ alkylthio, $C_1$ to $C_4$ alkyl-amino, di($C_1$ to $C_4$ alkyl)-amino or $C_1$ to $C_4$ alkyl-hydroxylamino radical, a phenylthio, phenylamino or phenoxy radical (which is optionally substituted by halogen, nitro, cyano, trifluoromethyl, $C_1$ to $C_4$ alkyl, $C_1$ to $C_4$ alkoxy, $C_1$ to $C_4$ alkylenedioxy, $C_1$ to $C_4$ alkylthio or $C_1$ to $C_4$ alkoxy-carbonyl), a 2,3-dihydro-2,2-dimethyl-7-benzofuranyl radical or a radical of the general formula

wherein
$R^7$ represents a hydrogen atom, or a $C_1$ to $C_4$ alkyl or di-($C_1$ to $C_4$ alkyl)-amino-carbonyl radical, and
$R^8$ represents a $C_1$ to $C_4$ alkyl, $C_1$ to $C_4$ alkylthio, cyano-$C_1$ to $C_4$ alkylthio or $C_1$ to $C_4$ alkylthio-$C_1$ to $C_4$ alkyl, or the two radicals $R^7$ and $R^8$ together represent $C_2$ to $C_8$ alkanediyl which is optionally interrupted by oxygen, sulphur, SO or $SO_2$, or
in which
Y represents a radical of the general formula

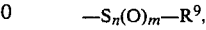

wherein
n is 1 or 2, and
m is 0, 1 or 2, and
$R^9$ represents an optionally halogen-substituted $C_1$ to $C_4$ alkyl, $C_3$ to $C_5$ alkenyl, $C_3$ to $C_5$ alkinyl or $C_3$ to $C_6$ cycloalkyl radical, or a benzyl, phenylethyl or phenyl radical (which is optionally substituted by halogen, cyano, nitro, trifluoromethyl, trifluoromethoxy, trifluoromethylthio, $C_1$ to $C_4$ alkyl or $C_1$ to $C_4$ alkoxy), or represents a radical of the general formula

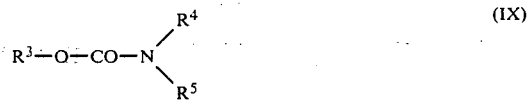

wherein
$R^{10}$ represents a $C_1$ to $C_4$ alkyl, $C_3$ to $C_5$ alkenyl, $C_3$ to $C_5$ alkinyl, $C_3$ to $C_6$ cycloalkyl or benzyl radical, and
$R^{11}$ represents a $C_1$ to $C_4$ alkyl, $C_3$ to $C_5$ alkenyl, $C_3$ to $C_5$ alkinyl, $C_3$ to $C_6$ cycloalkyl, benzyl, phenylethyl, halogenocarbonyl, formyl, $C_1$ to $C_4$ alkyl-carbonyl, $C_1$ to $C_4$ alkoxy-carbonyl, $C_1$ to $C_4$ alkoxyphenoxy-carbonyl, $C_3$ to $C_5$ alkinoxy-carbonyl, $C_3$ to $C_5$ alkenoxy-carbonyl, $C_1$ to $C_4$ alkylthio-carbonyl, $C_1$ to $C_4$ alkyl-amino-carbonyl, $C_1$ to $C_4$ alkyl-hydroxylamino-carbonyl, $C_1$ to $C_{10}$ alkyl-phenoxycarbonyl, di-($C_1$ to $C_4$ alkyl)-aminocarbonyl, phenylthiocarbonyl, phenoxycarbonyl or 2,3-dihydro-2,2-dimethyl-7-benzofuranyloxycarbonyl radical, or a phenylsulphinyl, phenylsulphonyl, phenyl or phenylsulphenyl radical (which is optionally substituted by halogen, cyano, nitro, trifluoromethyl, $C_1$ to $C_{10}$ alkyl or $C_1$ to $C_4$ alkoxy), or represents a radical of the general formula

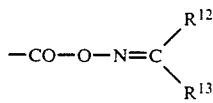

wherein $R^{12}$ has a meaning given above for $R^7$, and
$R^{13}$ has a meaning given above for $R^8$, and furthermore, in the radical of the general formula

the radicals $R^{10}$ and $R^{11}$ together represent a hydrocarbon chain which has 3 to 8 carbon atoms and is optionally interrupted by oxygen or sulphur, and wherein, furthermore, $R^9$ can also represent the same radical to which the radical $-S_n(O)_m-R^9$ is bonded.

Very particularly preferred active compounds of component (2) are carbamates of the formula (IX), in which $R^3$ represents a radical selected from phenyl, naphthyl, 2,3-dihydro-7-benzofuranyl, pyrazolyl and pyrimidinyl, which radical is optionally substituted by $C_1$ to $C_4$ alkyl, $C_2$ to $C_4$ alkenyl, $C_1$ to $C_4$ alkoxy, $C_1$ to $C_4$ alkoxy-methyl, $C_1$ to $C_4$ alkylthio, $C_1$ to $C_4$ alkylthiomethyl, $C_1$ to $C_4$ alkylamino, di-($C_1$ to $C_4$ alkyl)-amino, di-($C_3$ to $C_4$ alkenyl)-amino, halogen, dioxolanyl or methylenedioxy, and/or by the radical $-N=CH(CH_3)_2$,
or in which $R^3$ represents an alkylideneamino radical of the general formula

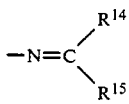

(IXa)

in which $R^{14}$ and $R^{15}$ have a meaning given above for $R^7$ and $R^8$ respectively, and $R^4$ represents a $C_1$ to $C_4$ alkyl radical, and $R^5$ represents a hydrogen atom or a $C_1$ to $C_4$ alkyl radical (preferably a hydrogen atom).

The following may be mentioned as examples of the carbamates of the formula (IX): 2-methyl-phenyl, 2-ethyl-phenyl, 2-iso-propyl-phenyl, 2-sec.-butyl-phenyl, 2-methoxy-phenyl, 2-ethoxy-phenyl, 2-iso-propoxy-phenyl, 4-methyl-phenyl, 4-ethyl-phenyl, 4-n-propyl-phenyl, 4-methoxy-phenyl, 4-ethoxy-phenyl, 4-n-propoxy-phenyl, 3,4,5-trimethyl-phenyl, 3,5-dimethyl-4-methylthio-phenyl, 3-methyl-4-dimethylamino-phenyl, 2-ethylthiomethyl-phenyl, naphth-1-yl, 2,3-dihydro-2,2-dimethyl-7-benzofuranyl, 2,3-(dimethyl-methylenedioxy)-phenyl, 2-(4,5-dimethyl-1,3-dioxolane-2-yl)-phenyl, 1-methylthio-ethylidene-amino, 2-methylthio-2-methylpropylideneamino-, 1-(2-cyano-ethylthio)-ethylideneamino- and 1-methylthiomethyl-2,2-dimethylpropylideneamino-N-methylcarbamate.

The synergistic action of the compounds of the formula (I), as component (1) is also preferably exhibited in the case of, as component (2), (B) carboxylates of the general formula

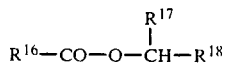

in which $R^{16}$ represents an open-chain or cyclic alkyl radical which is optionally substituted by halogen, alkyl or cycloalkyl, by alkenyl (which is optionally substituted by halogen, alkyl and/or alkoxy), by phenyl or styryl (which are optionally substituted by halogen or optionally halogen-substituted radical(s) selected from alkyl, alkoxy, alkylenedioxy and alkylthio), or by spirocyclically linked, optionally halogen-substituted cycloalk(ene)yl which is optionally benzo-fused,
and in which, furthermore, $R^{17}$ represents a hydrogen atom or an alkyl, halogenoalkyl, alkenyl, alkinyl or cyano radical, and $R^{18}$ represents an optionally substituted alkyl or aryl radical or a heterocyclic structure, or, together with $R^{17}$ and the carbon atom to which both radicals are bonded, forms a cyclopentenone ring.

Very particularly preferred active compounds of component (2) are carboxylates of the formula (X), in which $R^{16}$ represents a radical of the general formula

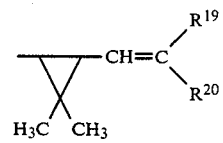

wherein $R^{19}$ represents a hydrogen, fluorine, chlorine or bromine atom or a methyl radical, and $R^{20}$ represents a methyl radical, a fluorine chlorine or bromine atom, a $C_1$ or $C_2$ fluoroalkyl or $C_1$ or $C_2$ chlorofluoroalkyl radical, or represents a phenyl radical (which is optionally substituted by halogen and/or by an optionally halogen-substituted radical(s) selected from $C_1$ to $C_4$ alkyl, $C_1$ to $C_4$ alkoxy, $C_1$ to $C_4$ alkylthio and $C_1$ or $C_2$ alkylenedioxy),
or wherein both radicals $R^{19}$ and $R^{20}$ represent a $C_2$ to $C_5$ alkanediyl (alkylene) radical;
or in which $R^{16}$ represents a radical of the general formula

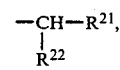

wherein $R^{21}$ represents a phenyl radical (which is optionally substituted by halogen and/or by optionally halogen-substituted radical(s) selected from $C_1$ to $C_4$ alkyl, $C_1$ to $C_4$ alkoxy, $C_1$ to $C_4$ alkylthio and $C_1$ or $C_2$ alkylenedioxy), and $R^{22}$ represents an isopropyl or cyclopropyl radical;
or in which $R^{16}$ represents one of the radicals

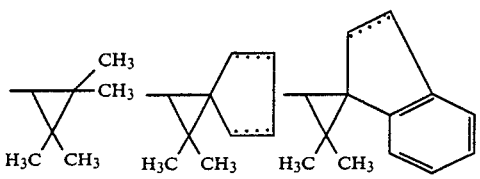

the dotted lines being intended to indicate possible double bonds, or represents a methyl radical,
and in which, furthermore, $R^{17}$ represents a hydrogen atom or a $C_1$ to $C_4$ alkyl, $C_1$ to $C_4$ halogenoalkyl, cyano or ethinyl radical, and $R^{18}$ represents an optionally halogen-substituted radical selected from phenyl, furyl and tetrahydrophthalimido, and this radical can in turn be substituted by halogen and/or by an optionally halogen-substituted radical selected from $C_1$ to $C_4$ alkyl, $C_2$ to $C_4$ alkenyl, $C_1$ to $C_4$ alkoxy, $C_2$ or $C_4$ alkenoxy, $C_1$ to $C_4$ alkylthio, $C_1$ or $C_2$ alkylenedioxy, phenoxy and benzyl, $R^{18}$ preferably representing pentafluorophenyl, 3,4-dichlorophenyl, or phenoxy-phenyl which can be substituted in one or both phenyl rings by halogen, or representing tetrahydrophthalimido.

Furthermore the naturally occurring pyrethroids (such as pyrethreum) are particularly preferred as carboxylates of the formula (X).

The following may be mentioned as examples of the carboxylates of the formula (X): 2,2,2-trichloro-1-(3,4-dichloro-phenyl)-ethyl acetate, 3,4,5,6-tetrahydrophthalimido-methyl 2,2-dimethyl-3-(2-methyl-propen-1-yl)-cyclopropane-carboxylate, 3-phenoxy-benzyl 2,2-dimethyl-3-(2,2-dichlorovinyl)-cyclopropane-carboxylate, α-cyano-3-phenoxy-benzyl 2,2-dimethyl-3-(2,2-dichlorovinyl)-cyclopropane-carboxylate, α-cyano-4-fluoro-3-phenoxy-benzyl 2,2-dimethyl-3-(2,2-dichlorovinyl)-cyclopropanecarboxylate, pentafluorobenzyl 2,2-dimethyl-3-(2,2-dichlorovinyl)-cyclopropanecarboxylate, α-cyano-3-phenoxy-benzyl 2,2-dimethyl-3-(2,2-dibromovinyl)-cyclopropanecarboxylate and α-cyano-3-phenoxy-benzyl 3-methyl-2-(4-chlorophenyl)-butanoate.

Furthermore, the synergistic action of the compounds of the general formula (I), as component (1) is preferably exhibited in the case of, as component (2)

(C) phosphates and phosphonates of the general formula

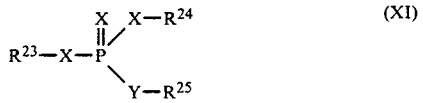

in which

X represents O or S in each case, and

Y represents O, S, —NH—, or a direct bond between the central P atom and $R^{25}$, and $R^{23}$ and $R^{24}$ are identical or different and represent an optionally substituted alkyl or aryl radical, and $R^{25}$ represents a hydrogen atom, an optionally substituted alkyl, aryl, heteroaryl, aralkyl, alkenyl or dioxanyl radical, or an oxime radical, or represents the same radical to which it is bonded.

Particularly preferred phosphates and phosphonates of the formula (XI) are those
in which $R^{23}$ and $R^{24}$ are identical or different and represent a $C_1$ to $C_4$ alkyl or phenyl radical, and $R^{25}$ represents a hydrogen atom, an alkyl radical which has 1 to 4 carbon atoms (and is optionally substituted by halogen, hydroxyl, cyano, optionally halogen-substituted phenyl, carbamoyl, alkylsulphonyl, alkylsulphinyl, alkylcarbonyl, alkoxy, alkylmercapto, alkoxycarbonyl or alkylaminocarbonyl; the latter having up to 6 carbon atoms in each case), or an alkenyl which has up to 4 carbon atoms (and is optionally substituted by halogen, optionally halogen-substituted phenyl or $C_1$ to $C_4$ alkoxycarbonyl), or represents a radical of the general formula

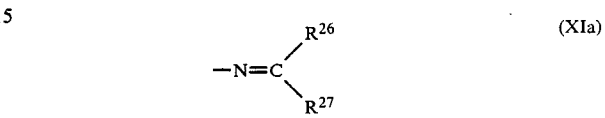

wherein $R^{26}$ and $R^{27}$ have a meaning given above for $R^7$ and $R^8$ respectively, or represents a cyano or phenyl radical, and in which $R^{25}$ furthermore represents a dioxanyl radical which is substituted by the same radical to which $R^{25}$ is bonded, or $R^{25}$ represents the same radical to which it is bonded, or $R^{25}$ represents a phenyl radical which is optionally substituted by methyl, nitro, cyano, halogen and/or methylthio), and $R^{25}$ in addition particularly preferably represents a heteroaromatic radical, such as pyridinyl, quinolinyl, quinoxalinyl, pyrimidinyl or benzo-1,2,4-triazinyl, which is optionally substituted by $C_1$ to $C_4$ alkoxy, $C_1$ to $C_4$ alkylthiomethyl, $C_1$ to $C_4$ alkyl and/or halogen.

The following may be mentioned individually: O,O-dimethyl or O,O-diethyl O-(2,2-dichloro- or 2,2-dibromo-vinyl)phosphate, O,O-diethyl O-(4-nitro-phenyl)thionophosphate, O,O-dimethyl O-(3-methyl-4-methylthio-phenyl)thionophosphate, O,O-dimethyl O-(3-methyl-4-nitro-phenyl)thionophosphate, O-ethyl S-n-propyl O-(2,4-dichlorophenyl)thionophosphate, O-ethyl S-n-propyl O-(4-methylthio-phenyl)thionophosphate, O,O-dimethyl S-(4-oxo-benzo-1,2,3-triazin-3-yl-methyl)thionothiolphosphate, O-methyl O-(2-iso-propyl-6-methoxy-pyrimidin-4-yl)thionomethanephosphonate, O,O-diethyl O-(2-iso-propyl-6-methyl-pyrimidin-4-yl)thionophosphate, O,O-diethyl O-(3-chloro-4-methyl-cumarin-7-yl)thionophosphate, O,O-dimethyl 2,2,2-trichloro-1-hydroxyethane-phosphonate and O,O-dimethyl S-(methylaminocarbonylmethyl)thionophosphate.

Furthermore, the synergistic action of the compounds of the general formula (I), as component (1), is preferably exhibited in the case of, as component (2), (D) halogeno(cyclo)-alkanes (such as hexachlorocyclohexane, 1,1,1-trichloro-2,2-bis-(4-chlorophenyl)-ethane, 1,1,1-trichloro-2,2-bis-(4-methoxyphenyl)-ethane and 1,1-dichloro-2,2-bis(4-ethylphenyl)-ethane).

The weight ratios of the active compounds in the active compound combinations can be varied within a relatively wide range. In general, the compound of the formula (I), of component (1) is employed together with the other active compound of component (2) in a mixing ratio, in parts by weight, of between 1:100 and 100:1, preferably between 1:5 and 5:1.

The active compound combinations according to the invention not only possess a rapid knock-down action, but also have a sustained effect in respect of the destruction of the arthropod pests, in particular of insects and mites, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compound combinations, comprising the compounds of the formula (I) as component (1) and the other active compound, as component (2), can be converted to the customary formulations, such as solutions, emulsions, wettable powders, suspensions, powders, dusting agents, foams, pastes, soluble powders, aerosols, suspension-emulsion concentrates, natural and synthetic materials impregnated with active compound, very fine capsules in polymeric substances, and formulations used with burning equipment, such as fumigating cartridges, fumigating cans and fumigating coils, as well as ULV cold mist and warm mist formulations.

These formulations may be produced in known manner, for example by mixing the active compound combinations with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dystuffs or metal phthalocyanine dyestuffs, and trace nutrients, such as salts of iron, manganese, boron, copper, cobalt, molybdenum and zinc.

The formulations in general contain from 0.1 to 95 percent by weight of active compound combination, preferably from 0.5 to 90 percent by weight.

The active compound combinations according to the invention are used in the form of their commercially available formulations and/or in the use forms prepared from these formulations.

The total active compound content (including the synergistic compound) of the use of forms prepared from the commercially available formulations can vary within wide limits. The active compound concentration of the use forms can be from 0.0001 to 100% by weight of the active compound combination, preferably between 0.01 and 10% by weight.

The compounds are employed in a customary manner appropriate for the use form.

When used against pests harmful to health and pests of stored products, the active compound combinations are distinguished by an excellent residual action on wood and clay as well as a good stability to alkali on limed substrates.

The present invention also provides pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids) which comprises applying to the pests, or to a habitat thereof, a compound combination of the present invention alone or in the form of a composition containing as active ingredient a compound combination of the present invention in admixture with a diluent or carrier.

The present invention further provides crops protected from damage by pests by being grown in areas in which immediately prior to and/or during the time of the growing a compound combination of the present invention was applied alone or in admixture with a diluent or carrier.

It will be seen that the usual methods of providing a harvested crop may be improved by the present invention.

The pesticidal activity of the compound combinations according to the invention is illustrated by the following biotest Example.

In this Example, the compounds of formula (I) to be used as component (1) in active compound combinations are each identified by a number given in brackets (except for compound (9) which is a known comparison compound), whereas the active compounds of component (2) are each identified by a capital letter given in brackets. The compounds concerned are identified as follows:

Active compounds to be used as component (2) of active compound combinations according to the invention

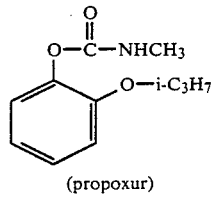

(propoxur) (A)

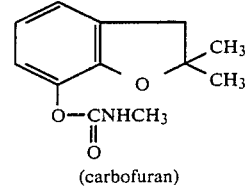

(carbofuran) (B)

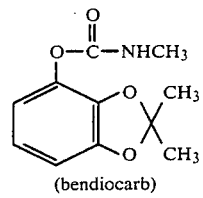

(bendiocarb) (C)

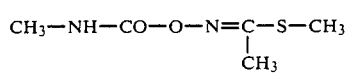

(methomyl) (D)

Pyrethrines of natural origin, as a 25% strength extract (E)

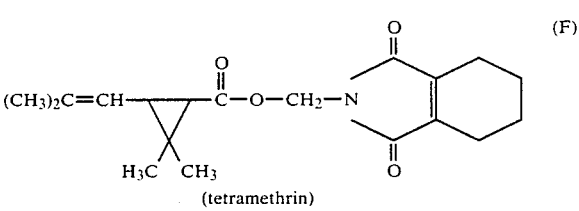

(tetramethrin) (F)

-continued

Active compounds to be used as component (2) of active compound combinations according to the invention

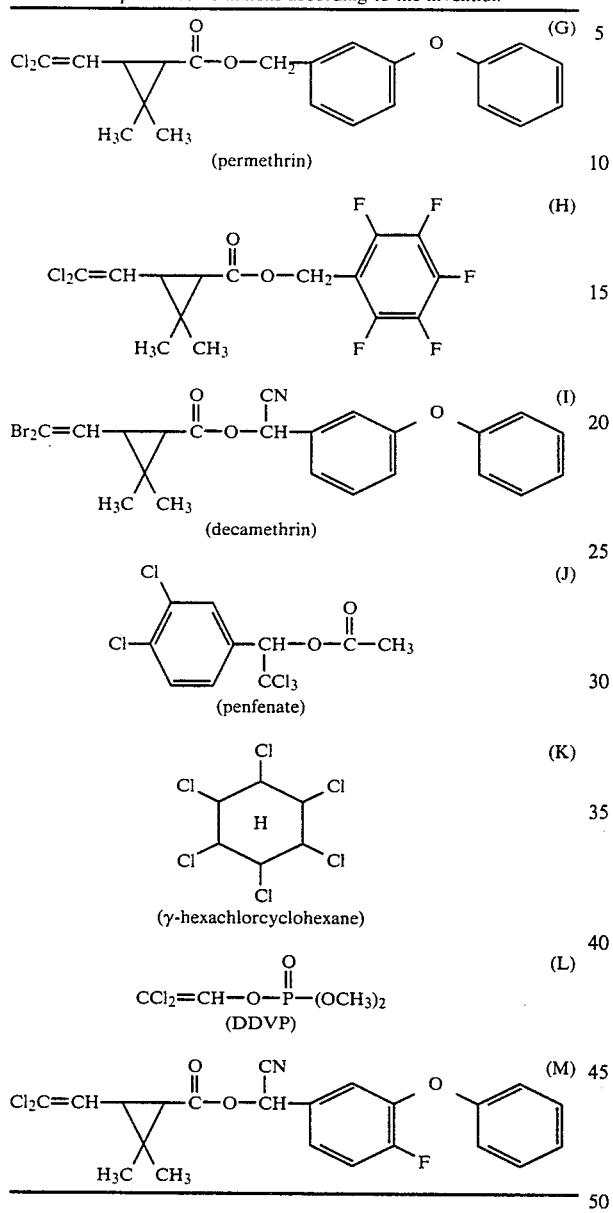

Synergistic compounds of formula (I) to be used as component (1) in active compound combinations according to the invention:

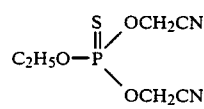 (1)

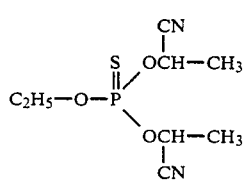 (2)

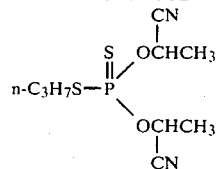 (3)

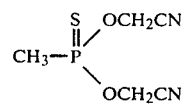 (4)

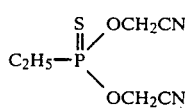 (5)

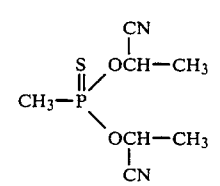 (6)

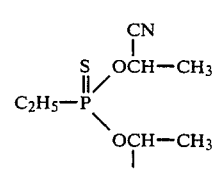 (7)

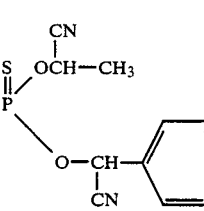 (8)

Comparative compound of the prior art

Piperonylbutoxide (known) (9)

EXAMPLES A $LT_{100}$ test

Test animals: Musca domestica (Weymanns strain) resistant to phosphoric acid esters and carbamates Solvent: Acetone Solutions were prepared from the active compounds, synergistic agents and mixtures of active compounds and synergistic agents, and 2.5 ml of the solutions were pipetted onto filterpaper discs of 9.5 cm diameter in Petri dishes. The filterpaper adsorbed the solutions. The Petri dishes were left standing open until the solvent had completely evaporated. 25 test animals were then introduced into the Petri dishes, and the dishes were covered with a glass lid.

The condition of the test animals was checked continuously for up to 6 hours. The time required for a 100% knock-down action was determined. If the $LT_{100}$ was not reached after 6 hours, the percentage of the test animals which had been knocked-down was determined.

The concentrations of the active compounds, synergistic agents and mixtures, and their actions, can be seen from the table which follows.

TABLE A

Test results
LT$_{100}$ test with Musca domestica (Weymanns strain) resistant to phosphoric acid esters

| Active compounds synergistic agents | Concentrations in % active compound/ synergistic agent | LT$_{100}$ in minutes, or in % at 360 minutes |
|---|---|---|
| (A) | 1.0 | 360' = 0% |
| (B) | 1.0 | 360' = 0% |
| (C) | 1.0 | 360' = 0% |
| (D) | 0.04 | 360' = 0% |
| (E) | 0.04 | 360' = 0% |
| (F) | 0.008 | 360' = 60% |
| (G) | 0.04 | 180' |
| (H) | 0.0016 | 60' |
| (I) | 0.04 | 45' |
| (J) | 1.0 | 360' = 70% |
| (K) | 0.008 | 360' |
| (L) | 0.008 | 360' = 95% |
| (M) | 0.04 | 60' |
| (1) | 1.0 | 360' = 0% |
| (2) | 1.0 | 360' = 0% |
| (3) | 1.0 | 360' = 0% |
| (4) | 1.0 | 360' = 0% |
| (5) | 1.0 | 360' = 0% |
| (6) | 1.0 | 360' = 0% |
| (7) | 1.0 | 360' = 0% |
| (8) | 1.0 | 360' = 0% |
| (9) (known) | 1.0 | 360' = 0% |
| (A) + (2) | 0.2 + 0.2 | 240' |
| (A) + (4) | 0.2 + 0.2 | 150' |
| (A) + (5) | 0.2 + 0.2 | 150' |
| (A) + (6) | 0.04 + 0.04 | 120' |
| (A) + (7) | 0.04 + 0.04 | 180' |
| (A) + (8) | 0.04 + 0.04 | 180' |
| (A) + (9) | 0.2 + 0.2 | 360' = 95% |
| (B) + (2) | 0.04 + 0.04 | 150' |
| (B) + (4) | 1.0 + 1.0 | 150' |
| (B) + (5) | 1.0 + 1.0 | 210' |
| (B) + (6) | 0.04 + 0.04 | 90' |
| (B) + (7) | 0.04 + 0.04 | 90' |
| (B) + (9) | 0.04 + 0.04 | 360' = 75% |
| (C) + (5) | 1.0 + 1.0 | 360' |
| (C) + (6) | 0.04 + 0.04 | 180' |
| (C) + (7) | 0.04 + 0.04 | 210' |
| (C) + (9) | 0.04 + 0.04 | 360' = 10% |
| (D) + (2) | 0.04 + 0.04 | 210' |
| (D) + (4) | 0.04 + 0.04 | 240' |
| (D) + (6) | 0.04 + 0.04 | 180' |
| (D) + (7) | 0.04 + 0.04 | 180' |
| (D) + (9) | 0.04 + 0.04 | 360' = 60% |
| (E) + (7) | 0.04 + 0.04 | 180' |
| (E) + (6) | 0.04 + 0.04 | 180' |
| (F) + (2) | 0.008 + 0.008 | 180' |
| (F) + (3) | 0.008 + 0.008 | 150' |
| (F) + (6) | 0.008 + 0.008 | 120' |
| (F) + (7) | 0.008 + 0.008 | 180' |
| (F) + (9) | 0.008 + 0.008 | 360' = 10% |
| (G) + (1) | 0.04 + 0.04 | 90' |
| (G) + (2) | 0.04 + 0.04 | 105' |
| (G) + (3) | 0.04 + 0.04 | 150' |
| (G) + (4) | 0.04 + 0.04 | 90' |
| (G) + (5) | 0.04 + 0.04 | 120' |
| (G) + (6) | 0.04 + 0.04 | 105' |
| (G) + (7) | 0.04 + 0.04 | 90' |
| (H) + (2) | 0.0016 + 0.0016 | 45' |
| (H) + (3) | 0.0016 + 0.0016 | 45' |
| (H) + (6) | 0.0016 + 0.0016 | 45' |
| (H) + (7) | 0.0016 + 0.0016 | 45' |
| (I) + (3) | 0.04 + 0.04 | 30' |
| (I) + (6) | 0.04 + 0.04 | 30' |
| (I) + (7) | 0.04 + 0.04 | 30' |
| (J) + (1) | 0.2 + 0.2 | 240' |
| (J) + (2) | 0.2 + 0.2 | 240' |
| (J) + (5) | 0.2 + 0.2 | 180' |
| (J) + (7) | 0.2 + 0.2 | 210' |

TABLE A-continued

Test results
LT$_{100}$ test with Musca domestica (Weymanns strain) resistant to phosphoric acid esters

| Active compounds synergistic agents | Concentrations in % active compound/ synergistic agent | LT$_{100}$ in minutes, or in % at 360 minutes |
|---|---|---|
| (J) + (9) | 0.2 + 0.2 | 360' = 95% |
| (K) + (1) | 0.008 + 0.008 | 150' |
| (K) + (2) | 0.008 + 0.008 | 120' |
| (K) + (3) | 0.008 + 0.008 | 150' |
| (K) + (4) | 0.008 + 0.008 | 210' |
| (K) + (5) | 0.008 + 0.008 | 120' |
| (K) + (6) | 0.008 + 0.008 | 120' |
| (K) + (7) | 0.008 + 0.008 | 150' |
| (K) + (9) | 0.008 + 0.008 | 180' |
| (L) + (1) | 0.008 + 0.008 | 180' |
| (L) + (4) | 0.008 + 0.008 | 210' |
| (L) + (7) | 0.008 + 0.008 | 105' |
| (L) + (9) | 0.008 + 0.008 | 360' = 85% |
| (M) + (3) | 0.04 + 0.04 | 45' |
| (M) + (6) | 0.008 + 0.008 | 45' |
| (M) + (7) | 0.04 + 0.04 | 45' |

The preparative examples which follow illustrate the preparation of the compounds of the formula (I):

Preparative Examples

EXAMPLE 1

Reaction variant (a)

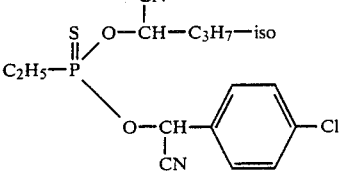

14.1 g (0.1 mol) of 4-chlorobenzaldehyde, 22.6 g (0.1 mol) of O-(1-cyano-2-methyl-propyl)-ethyl-thiophosphonic acid ester-chloride, 0.6 g of tetrabutylammonium bromide and 5.6 g (0.12 mol) of sodium cyanide in 300 ml of toluene were initially introduced, and 10 ml of water were added dropwise at an internal temperature between 0° and 10° C., while stirring vigorously. After the end of the addition, the temperature was slowly increased to 20° C., and stirring was continued until the end of the reaction. Thereafter, the aqueous phase was separated off, and the organic phase was washed with twice 100 ml of water and dried over sodium sulphate. After the solvent had been stripped off under the vacuum from a water jet, and sparingly volatile constituents had been distilled off at 50° C./3 mm Hg, 31 g (86.9% of theory) of O-(1-cyano-1-(4-chlorophenyl)-methyl) O-(1-cyano-2-methyl-propyl)ethyl-thiophosphonate of refractive index n$_D^{20}$: 1.5357 were obtained as an oily residue.

EXAMPLE 2

Reaction variant (b)

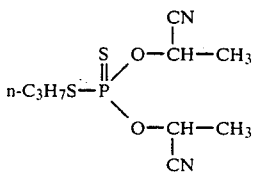

(Synergistic agent No. (3))

20.9 (0.1 mol) of S-n-propyl-dithiophosphoric aciddichloride, 13.2 g (0.3 mol) of acetaldehyde, 11.2 g (0.23 mol) of sodium cyanide and 1 g of tetrabutylammonium bromide in 200 ml of hexane were initially introduced, and 20 ml of water were added dropwise at an internal temperature between 0° and 5° C., while stirring vigorously. After the end of the addition, the temperature was slowly increased to 20° C., and stirring was continued until the end of the reaction. After the organic phase had been separated off, the residue was extracted with twice 200 ml of methylene chloride, and the combined organic phases were washed twice with 100 ml of water and dried over sodium sulphate. After the solvent had been stripped off under the vacuum from a water jet, and sparingly volatile constituents had been distilled off at 50° C./3 mm Hg, 19.4 g (70% of theory) of bis-O,O-(1-cyano-ethyl) S-n-propyl dithiophosphate of refractive index $n_D^{20}$: 1.5013 were obtained as an oily residue.

EXAMPLE 3

Reaction variant (c)

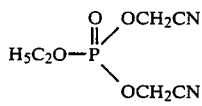

64 g (0.2 mol) of a 15% strength solution of butyllithium in hexane were added dropwise to a solution of 22.8 g (0.4 mol) of hydroxyacetonitrile in 200 ml of ether/tetrahydrofuran (1:1) at −78° C. This mixture was then added dropwise to a solution of 16.3 g (0.1 mol) of O-ethylphosphoric acid ester-dichloride in 50 ml of tetrahydrofuran at −50° C. After the end of the addition, the mixture was warmed to 20° C., and stirring was continued at this temperature for 12 hours. After the solvent had been removed under the vacuum from a water jet, the residue was taken up in methylene chloride, the solution was washed with water, and the organic phase was dried over sodium sulphate. 3.8 g (20% of theory) of bis-O,O-(cyano-methyl) O-ethyl phosphate of boiling point 146° C./0.5 mm Hg and refractive index $n_D^{20}$: 1.4325 were obtained after distillation.

The compounds of the formula (I) which are listed in the table below could be prepared analogously to reaction variants (a) or (b), or (c), respectively:

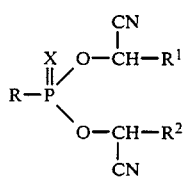   (I)

TABLE 2

| Example No. | X | R | R¹ | R² | Physical data refractive index $n_D^{20}$ | Synergistic agent No. |
|---|---|---|---|---|---|---|
| 4 | S | —OC₂H₅ | —CH₃ | —CH₃ | 1.4702 | (2) |
| 5 | S | —CH₃ | —CH₃ | —CH₃ | 1.4770 | (6) |
| 6 | S | —C₂H₅ | —CH₃ | —C₆H₄Cl | 1.5262 | (8) |
| 7 | S | —OC₂H₅ | —C₆H₄Cl | —CH₃ | 1.4280 | |
| 8 | S | —C₆H₅ | i-C₃H₇ | —CH₃ | 1.5190 | |
| 9 | S | —OC₂H₅ | H | H | 1.4863 | (1) |
| 10 | S | —CH₃ | H | H | 1.5100 | (4) |
| 11 | S | —C₂H₅ | H | H | 1.4993 | (5) |
| 12 | S | —C₂H₅ | —CH₃ | —CH₃ | 1.4783 | (7) |
| 13 | O | —C₂H₅ | H | H | 1.4500 | |

The example which follows illustrates the preparation of starting compounds of the formula (II):

EXAMPLE 14

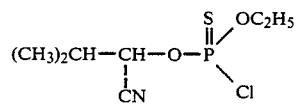

233 g (1.3 mol) of O-ethyl-thiophosphoric acid ester-dichloride, 72 g (1.0 mol) of isobutyraldehyde and 6 g of tetrabutylammonium bromide in 1 liter of hexane were initially introduced, and a solution of 56 g (1.1 mol) of sodium cyanide in 100 ml of water was added dropwise at an internal temperature between 0° C. and 5° C., while stirring vigorously. After the end of the addition, the temperature was slowly increased to 20° C., and the mixture was stirred for a further 12 hours. Thereafter, the aqueous phase was separated off, and the organic phase was washed with 100 ml of water and dried with sodium sulphate. After the solvent had been stripped off under the vacuum from a water jet, and the excess starting material had been distilled off, 173 g (71% of theory) of O-ethyl-O-(1-cyano-2-methyl-propyl)-thiophosphoric acid diester-chloride were obtained as an oily residue of refractive index $n_D^{20}$: 1.4806.

The remaining starting compounds of the formula (II) could also be prepared analogously to this Example.

We claim:

1. An arthropodicidal composition comprising an arthopodicidally effective amount of (1) a dicyanohydrin (thiono)(dithio)-phosphate or phosphonate of the formula

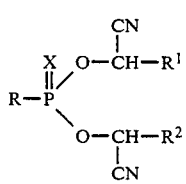

in which

X represents oxygen or sulphur,

R represents an optionally halogen-substituted radical selected from the group consisting of $C_1$ to $C_5$ alkyl, $C_2$ to $C_5$ alkenyl, $C_2$ to $C_5$ alkinyl, phenyl, benzyl, $C_1$ to $C_5$ alkoxy, phenoxy, benzyloxy, $C_1$ to $C_5$ alkylthio, phenylthio, benzylthio, mono- or di-($C_1$ to $C_5$ alkyl)-amino, phenylamino and benzylamino, and $R^1$ and $R^2$ are identical or different and individually represent a hydrogen atom, an alkyl radical which has 1 to 20 carbon atoms which is optionally substituted by halogen, cyano, $C_1$ to $C_4$ alkoxy or $C_1$ to $C_4$ alkylthio, an optionally halogen-substituted $C_2$ to $C_5$ alkenyl or $C_2$ to $C_5$ alkinyl radical, a $C_3$ to $C_8$ cycloalkyl radical which is optionally substituted by $C_1$ to $C_4$ alkyl, $C_1$ to $C_4$ alkoxycarbonyl, phenoxybenzyloxycarbonyl or halogen, a phenyl-$C_1$ to $C_4$ alkyl radical which is optionally substituted by halogen, $C_1$ to $C_4$ alkyl or $C_1$ to $C_4$ alkoxy, a phenyl radical which is optionally substituted by halogen, cyano, nitro, $C_1$ to $C_4$ alkyl, $C_1$ to $C_4$ alkoxy, $C_1$ to $C_4$ alkylthio, trifluoromethyl or by optionally halogen-substituted $C_1$ or $C_2$ alkylenedioxy, a furyl, a thienyl or a pyridyl radical, and (2) an arthropodicidally effective amount of an insecticide selected from the group consisting of a (A) carbamate, (B) carboxylate, (C) phosphate or phosphonate other than (1), and (D) halogeno-(cyclo)-alkene, the weight ratio of (1):(2) being from about 1:100 to 100:1.

2. A composition according to claim 1, wherein (2) is a carbamate.

3. A composition according to claim 1, in which

X represents oxygen or sulphur,

R represents an optionally fluorine-substituted or optionally chlorine-substituted radical selected from the group consisting of $C_1$ to $C_5$ alkyl, phenyl, $C_1$ to $C_5$ alkoxy, phenoxy, benzyloxy, $C_1$ to $C_5$ alkylthio, phenylthio, benzylthio and mono- or di-($C_1$ to $C_5$ alkyl)-amino and $R^1$ and $R^2$ are identical or different and individually represent a hydrogen atom, an alkyl radical which has 1 to 10 carbon atoms which is optionally substituted by fluorine, chlorine, methoxy or methylthio, a $C_2$ to $C_5$ alkenyl, $C_3$ to $C_6$ cycloalkyl radical, an optionally chlorine-substituted phenyl-$C_1$ or $C_2$ alkyl radical, a phenyl radical which is optionally substituted by fluorine, chlorine, cyano, nitro, methyl, methoxy, trifluoromethyl or methylenedioxy, a thienyl or a pyridyl radical.

4. A composition according to claim 1, in which X is sulphur.

5. A composition according to claim 1, wherein (1) is bis-(1-cyano-ethyl)methylthionophosphonate of the formula

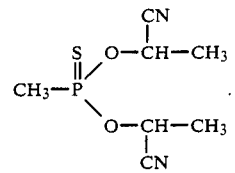

6. A composition according to claim 5, wherein (2) is 2-isopropoxyphenyl N-methyl-carbamate of the formula

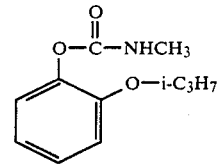

7. A composition according to claim 5, wherein (2) is 2,3,4,5,6-pentafluorobenzyl 3-(2,2-dichlorovinyl)-2,2-dimethylcyclopropanecarboxylate of the formula

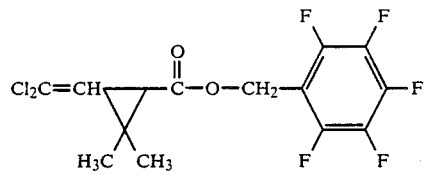

8. A composition according to claim 5, where (2) is O-(2,2-dichlorovinyl)-O,O-dimethyl-phosphate of the formula

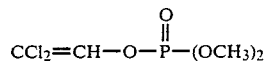

9. A composition according to claim 5, wherein (2) is α-cyano-4-fluoro-3-phenoxy-benzyl 3-(2,2-dichlorovinyl)-2,2-dimethyl-cyclopropanecarboxylate of the formula

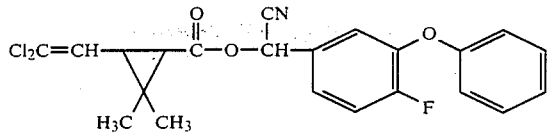

10. A method of combating arthropods which comprises administering to such arthropods or to an arthropod habitat an arthropodicidally effective amount of a composition according to claim 1.

11. A method according to claim 10, wherein (1) is bis-O,O-(1-cyano-ethyl)methylthionophosphoante and (2) is 2-isopropoxyphenyl N-methyl-carbamate,
2,3,4,5,6-pentafluorobenzyl 3-(2,2-dichlorovinyl)-2,2-dimethyl-cyclopropanecarboxylate,
O-(2,2-dichlorovinyl)-O,O-dimethyl-phosphate or
α-cyano-4-fluoro-3-phenoxy-benzyl 3-(2,2-dichlorovinyl)-2,2-dimethyl-cyclopropanecarboxylate.

* * * * *

UNITED STATES PATENT AND TRADEMARK OFFICE
CERTIFICATE OF CORRECTION

PATENT NO. : 4,511,562

DATED : April 16, 1985

INVENTOR(S) : Bernd-Wieland Krüger, et al

It is certified that error appears in the above-identified patent and that said Letters Patent is hereby corrected as shown below:

| | |
|---|---|
| 1st Page, Title, line 1, and Col. 1, line 2 | Delete "(THIO)" and substitute --(THIONO)-- |
| Col. 2, line 57 | After "above," delete "the" and substitute --and-- |
| Col. 5, line 51 | Correct spelling of "reaction" |
| Col. 16, line 22 | Delete "represents" and substitute --respresent-- |
| Col. 25, line 11 | After "acid" insert -- - -- |
| Col. 27, line 66 | After "bis-" insert --O,O- -- |

Signed and Sealed this

Tenth Day of September 1985

[SEAL]

Attest:

DONALD J. QUIGG

Attesting Officer    Acting Commissioner of Patents and Trademarks - Designate